United States Patent [19]

Davis

[11] Patent Number: 5,169,251
[45] Date of Patent: Dec. 8, 1992

[54] HAND-WORN DISPENSER

[76] Inventor: Sharron L. Davis, 2520 N. 12th St., Quincy, Ill. 62301

[21] Appl. No.: 740,060

[22] Filed: Aug. 5, 1991

[51] Int. Cl.⁵ .......................... A46B 5/04; B43K 5/14; B05C 11/00
[52] U.S. Cl. ....................................... 401/7; 401/132; 401/266
[58] Field of Search ........................ 401/6-8, 401/28, 132, 37, 265, 266; 604/292, 289, 304-308

[56] References Cited

U.S. PATENT DOCUMENTS

| | | | |
|---|---|---|---|
| 671,296 | 4/1901 | Rowand | 401/7 |
| 1,481,772 | 1/1924 | Zell | 401/7 |
| 2,044,428 | 6/1936 | Gilmer | 401/7 X |
| 2,157,543 | 5/1939 | Kingman | 401/8 X |
| 2,771,224 | 11/1956 | Boerger | 401/8 X |
| 3,116,732 | 1/1964 | Cahill | 604/306 X |
| 3,473,699 | 10/1969 | Pike | 401/7 X |
| 3,778,172 | 12/1973 | Myren | 401/7 |
| 3,806,260 | 4/1974 | Miller | 401/132 X |
| 3,883,897 | 5/1975 | Lefkowitz | 401/7 X |
| 4,127,339 | 11/1978 | Malacheski | 401/132 |
| 4,911,688 | 3/1990 | Jones | 604/305 X |
| 4,917,688 | 4/1990 | Nelson | 604/306 |

Primary Examiner—Danton D. DeMille
Attorney, Agent, or Firm—Joseph W. Holloway

[57] ABSTRACT

A thin-walled protective glove having a self-contained palmar receptacle for storing various materials to be dispensed from the receptacle in response to the wearer's compressing or otherwise agitating the receptacle. The receptacle displays tributary conduits extending along the glove fingers to the fingertips and such conduits may have distal terminations through which materials are supplied to and dispensed from the receptacle. The receptacle and conduits may have perforations covered with sealing strips which are selectively removable to permit dispensing of stored material therethrough.

1 Claim, 3 Drawing Sheets

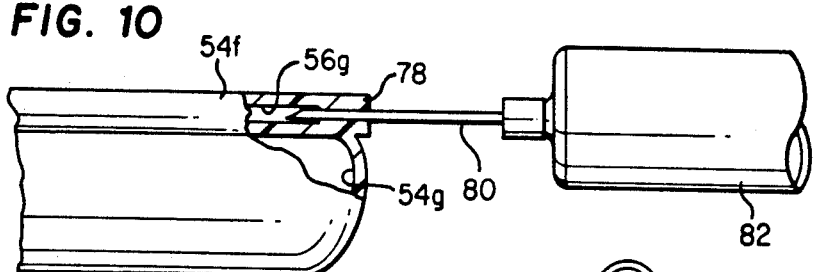
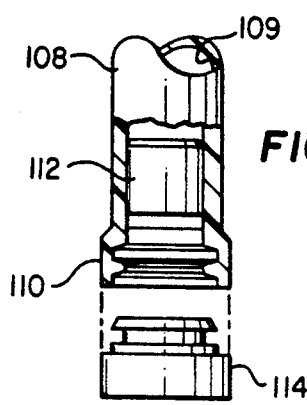
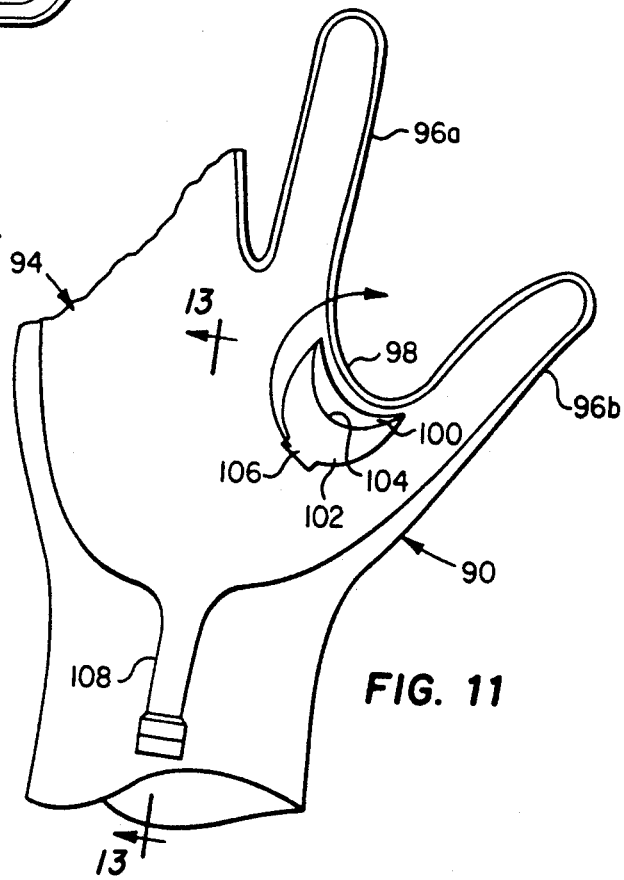
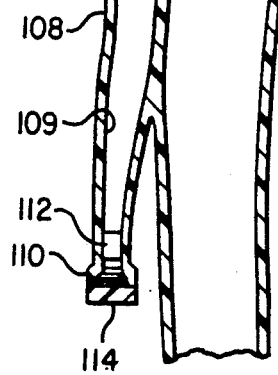

HAND-WORN DISPENSER

BACKGROUND OF THE INVENTION

This invention generally relates to a hand-worn dispenser comprising a thin-walled glove equipped with a self-contained receptacle for storing dry particulate or liquid material intended to be dispensed from the glove in response to the wearer's squeezing or otherwise agitating the receptacle with his hand.

In accordance with the teaching of this invention, the rate of substance delivery may be selected and the directionality of substance flow outside the dispenser glove may be carefully controlled. Several glove dispensers and applicators which do not display such desirable features are disclosed in the prior patent art. For example, mittens intended for use as wash cloths for bathing purposes and having soap disposed in a water-permeable palm-located pocket are disclosed in U.S. Pat. No. 674,913 to Fike and in U.S. Pat. No. 1,766,365 to Weiss et al. Multilayered mitts or gloves for applying various substances contained between an inner skin protective layer and an outer porous layer are shown in U.S. Pat. No. 993,662 to Dueease (cleaning powder), U.S. Pat. No. 1,046,230 to Springhorn (powdered stove polish), U.S. Pat. No. 1,161,719 to Norton (skin massage tonic), and U.S. Pat. No. 3,701,604 to Holroyd (liquid herbicide).

Norton discloses separate liquid receptacles associated with each of the finger tips of a protective glove. U.S. Pat. No. 3,778,172 to Myren teaches a mitt displaying a liquid receptacle located generally centrally of the wearer's palm. The reservoir pockets of Fike and Springhorn cover the entire palm and undersides of the fingers. U.S. Pat. No. 3,473,699 to Pike shows a three-layered glove defining a perforated powder chamber extending from the wrist to the fingertips of the wearer.

The materials stored in the receptacles of the prior art mitts and gloves are usually discharged by squeezing the receptacles with the hand or by rubbing, pressing or impacting the glove or mitt directly against the object which receives the dispensed material. Discharged material passes through a permeable or porous area of the glove or through an array of small perforations provided for this purpose. Usually, material discharge from prior art glove applicators occurs over the greater part of the palmar side of the glove in an uncontrollable and uneven manner. Such eratic discharge of material is characteristic of the prior art and precludes the use of handworn dispensers in those application where a carefully controlled material discharge rate is desirable or essential. Moreover, none of the prior art devices suggest a dispensing glove structure capable of producing a highly directional stream of glove-contained substance for application to an object without the glove's coming into contact with the object.

Another structural and operational shortcoming of prior art glove dispensers and applicators is their lack of efficient means for filling and sealing a storage reservoir defined by the glove with a wide variety of kinds of materials such as, for example, skin lotion, pet shampoo, cleaning powder and liquid, semi-liquid burn medication, lubricating grease and oil, hair coloring and bleaching solution, insect repellant, adhesive, etc. This problem is exacerbated if the reservoir is to be filled with substances which are irritating to the skin, or substances which must be kept sterile or otherwise free from contamination, or substances which soil or discolor if spilled. If a glove is intended to be refilled from time to time by the glove user, the need for simple yet effective means to accomplish the filling function is expecially desirable.

While each of the abovecited glove dispensers is useful exclusively for applying either a dry powder (Dueease, Springhorn and Pike) or a liquid solution (Fike, Weiss et al, Norton, Holbroyd and Myren), none recognized the advantages of utilizing the same general glove configuration to dispense both dry and wet substances.

SUMMARY OF THE INVENTION

The general object of this invention is to provide a novel dispenser which is structurally and operationally adapted to overcome the aforenoted shortcomings of prior devices intended for the same purpose.

A principal object is to provide a handworn glove dispenser which includes a selfcontained reservoir or receptacle fillable with various substances and materials which can be conveniently stored therein until dispensed for their intended uses. The dispenser according to this invention covers and protects the user's palm area and fingers in the manner of a conventional glove. The palmar surface of the reservoir comprises an overlayer of glove material attached to and covering portions of the palm and finger areas of the underlying glove body. In a preferred embodiment, the hand-receiving portion of the glove and the fillable reservoir are integrally formed by a single molding operation which produces a suitably thin and flexible glove body.

The utility and desirability of handworn dispensers are vastly increased by these key features of this invention; namely, 1. A rate of material discharge from the glove's reservoir can be established by individual users over a wide range to accommodate the requirements of very different dispensed materials and applications; and,
2. The material is discharged from the reservoir through user selectable openings located in various portions of the glove whereby the pattern and direction of material flow from the glove reservoir is controllable.

As will be described hereinafter, these important advantages are produced in a novel glove construction wherein the material reservoir, which is located in the plamar area of the glove, communicates with tributary channels extending along the underside of the glove fingers outwardly toward the fingertips. The palmar surface and outwardly extending undersurfaces of the fingers may be perforated to provide means for discharging material from the reservoir; and, this invention contemplates that removable strips cover and seal the perforations until they are selectively removed by the user. Alternatively, the reservoir and the finger tributaries may be completely sealed and the extreme ends of the tributaries located at the glove fingertips are then selectively opened, by various means hereinafter described, to provide one or more discharge openings remote from the palmar reservoir. Such fingertip discharge openings provide the user a unique ability to apply dispensed material by merely positioning his fingertips or fingers on or proximate the point or area to be treated.

Yet another important object of this invention is the provision of improved means for filling or charging the reservoirs or material receptacles of the glove dispensers. To this end, the main palmar receptacle may exhibit a sizeable filling aperture which after filling is sealable by an overlying flap of glove material. Alternatively, the reservoir may be equipped with a projecting filler tube having a one-way flow control valve to receive material under pressure into the reservoir interior. Reservoir filling may also take place through the aforementioned finger tributary channels by means of a typical syringe needle penetrating the channel wall or by means of a filler tube coupled with a fitting carried by the projecting end of a finger channel. As will be more fully understood after considering the following specification, the choice of reservoir filling means should be selected for a particular glove configuration taking into consideration such factors as the skill and care needed to fill the reservoir, the handling characteristics of the dispensable substance which may dictate a preferred filling means, any requirement that the dispensible substance and/or the glove be sterile at the time of use, whether the glove will be on or off the user's hand when filling takes place, and the means by which the material is to be dispensed from the glove.

Still another specific object of this invention is the provision of a glove dispenser wherein two or more component ingredients may be conveniently introduced into the glove reservoir to form a resultant combination that is to be dispensed. Also provided is a plural-chambered receptacle from which isolated materials are serially or simultaneously dispensable through separate discharge means for subsequent mixing or reaction outside the glove or for applying such isolated materials to different objects outside the glove.

Another general object is to provide a dispenser glove which may be fabricated of inexpensive natural or man-made materials using conventional manufacturing technics.

These and other advantages and objects of this invention and the manner of obtaining them will be best appreciated and fully understood by having reference to the following detailed description of the preferred embodiments of the invention taken in conjunction with the accompanying drawings.

DESCRIPTION OF THE DRAWINGS

FIG. 10 shows a syringe needle penetrating the terminal end wall of the reservoir tributary shown in a partial sectional view taken along lines 10—10 of FIG. 2;

FIG. 11 depicts a glove fragment including a projecting filling tube as well as a crescent shaped filling aperture closable by means of a flap-like seal;

FIG. 12 is a perspective view of the glove shown in FIG. 11 wherein the filling flap has been drawn over the filling aperture and pressed into sealed engagement with the outer glove surface;

FIG. 13 is an enlarged partial sectional view taken generally along lines 13—13 of FIG. 11; and, FIG. 14 is an enlarged sectional view of the filler tube and valve shown in FIG. 13.

DETAILED DESCRIPTION OF THE INVENTION

Figure 1:
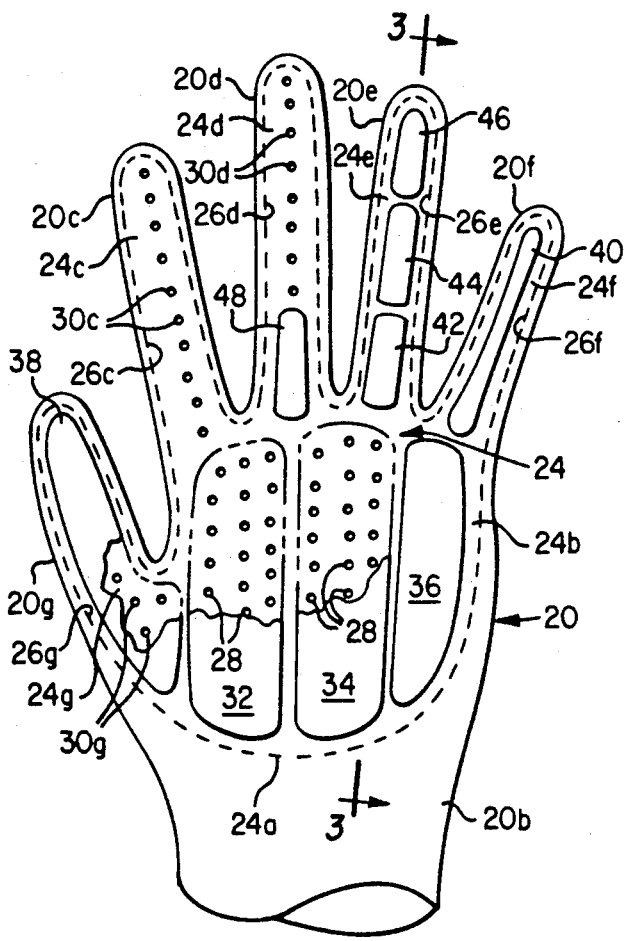
FIG. 1 is a plan view of the palm side of a lefthand glove dispenser according to this invention wherein a palmar reservoir having finger tributaries is outlined in broken lines; and, variously shaped sealing strips, some of which are partially broken away, overly and seal a series of perforations opening from the palm reservoir and finger tributaries of the glove.
Figure 3:
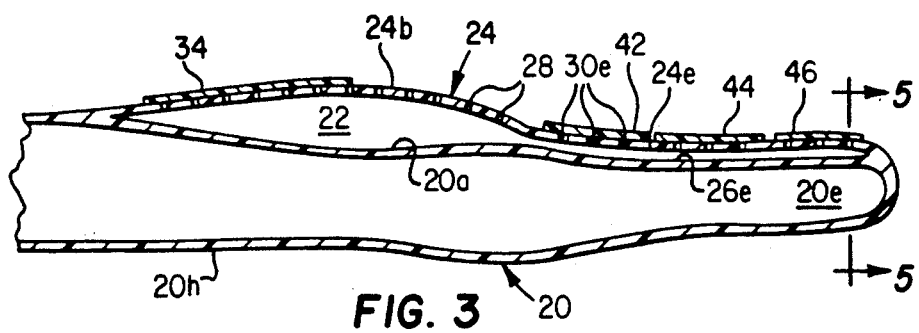
FIG. 3 is a sectional view taken generally along lines 3—3 of FIG. 1.

FIGS. 1 and 3 of the drawings illustrate a dispenser according to this invention comprising a hand-receiving glove body 20 having a substance receptacle 22 generally overlying the glove palm 20a. The glove body 20 itself is conventionally constructed and has in addition to the palm 20a, a wrist portion 20b, finger pockets 20c, 20d, 20e and 20f, a thumb pocket 20g and a back portion 20h. The receptacle 22 is generally palmate and is defined by an overlayer or outer face 24 superjacent the glove's surface 20a and the inner surfaces of the finger and thumb pockets. This overlayer, denoted in its entirety by numeral 24, is best illustrated in FIG. 1 where its peripheral margin 24a is shown in broken lines. The palmar portion 24b of the overlayer 24 is disposed in overlying juxtaposition with the glove palm 20a and, in the embodiment shown in FIG. 1, covers the glove palm substantially from side to side and from its heel to the base of the fingers and thumb. The overlayer 24 also has finger extensions 24c through 24f and a thumb-shaped extension 24g disposed in overlying juxtaposition with corresponding finger or thumb pockets; and, as seen in FIGS. 1 and 5, the various finger extensions and their corresponding pockets are of substantially the same width.

Figure 5:
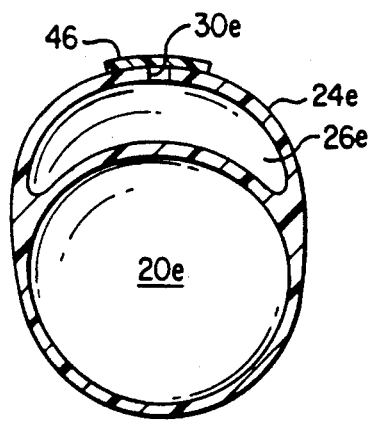
FIG. 5 is an enlarged cross sectional view taken along liens 5—5 of FIG. 3.

As will be best understood from viewing FIGS. 3 and 5, the fingers of the glove 20 and the finger extensions of the overlayer 24 are integrally joined at their sides to define conduits or tributaries therebetween leading from the receptacle 22 and traversing the underside of the fingers to the fingertips of the glove. FIGS. 3 and 5 show one of these conduits at numeral 26e; however, it will be understood that similarly defined conduits, 26c 26d, 26f and 26g shown in broken lines in FIG. 1, extend along the entire length of the other finger and thumb pockets 20c, 20d, 20f and 20g. As will be understood from viewing FIG. 5, the conduit 26e, as well as the other finger conduits extend fully across the glove finger 20e and displays a flattened, crescent-like cross section. These finger conduits or reservoir tributary channels also have a substantial cross-sectional area for a reason and purpose to be described hereinafter.

The overlayer 24, as depicted in FIGS. 1 and 3, has a series of perforations extending through its major palmar portion 24b and through each of its finger extensions 24c through 24g. The perforations 28 are arrayed to cover substantially all of the overlayer portion 24b which in part defines the palm receptacle 22. Perforations 30c through 30g are spaced along the finger extensions from the points of their connections with the palmar overlayer portion 24b to their distal ends or tips. The perforations 28 and 30 function respectively as dispensing outlets from the palm receptacle 22 and from the finger conduits 26c through 26g. As will be more fully explained, the size, number and placement of the perforations are variable depending on the type of material being dispensed by the glove 20 and on the desired discharge flow pattern.

One of the principal objects and advantages of this invention, namely, control of the rate and the location of the discharge of dispensed material from the glove 20, is achieved by the provision of means for sealing selected groups of the aforedescribed material discharge perforations. FIG. 1 shows a plurality of discrete sealing strips of various shapes and sizes overlying the palm receptacle 24b and the finger conduits 26c through 26g. The sealing strips are removably secured to the exposed surface of the overlayer 24 by any suitable means such as a thin layer of pressure sensitive adhesive on the underside of the strips. The thickness of the sealing strips may be the same or slightly less than that of the glove body 20 and the overlayer 24 so that they flex easily and may be removed by lifting an edge and peeling them away. The size and shape of the various strips may be varied as desired to seal off discharge perforations in groups of a selected number and location. For example, three separate strips 32, 34 and 36, as shown in FIG. 1, are employed to seal all of the palm receptacle discharge openings 28 in three laterally spaced groups extending across the overlayer palm portion 24b. The thumb conduit 26g and the small finger conduit 26f are illustrated as having all of their discharge perforations sealed by single elongated strips 38 and 40, respectively. The finger conduit 26e shown in FIGS. 1, 3 and 5 has all of its discharge perforations 30e closed by three separate strips 42, 44 and 46 spaced longitudinally from the base of the overlayer finger extension 24e to its tip. For purposes of illustration only, the index finger discharge perforations 30c and the greater portion of the middle finger perforations 30d are shown with their sealing strips removed. One group of those discharge perforations 30d at the base of the overlayer finger extension 24d remain closed by a strip segment 48.

It is contemplated that the dispenser glove 20 will have all dispenser perforations closed by various sealing strips of the type disclosed before the dispenser is filled and furnished to the user. It should be understood that the size and shape of the seal strips may be varied as desired so that selected groups of perforations or perhaps only a single perforation may be conveniently opened. For example, the palm covering strips 32, 34 and 36 may be combined into a single large peel-off strip or, one elongate strip could be employed to seal all of the index finger perforations 30c except a single perforation adjacent the distal end of the conduit 26c which would have its own small sealing tab, not shown.

Figure 4:
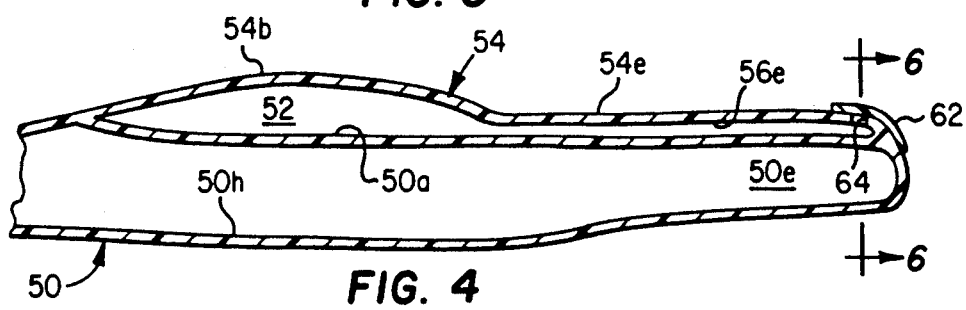
FIG. 4 is a sectional view taken generally along lines 4—4 of FIG. 2.
Figure 2:
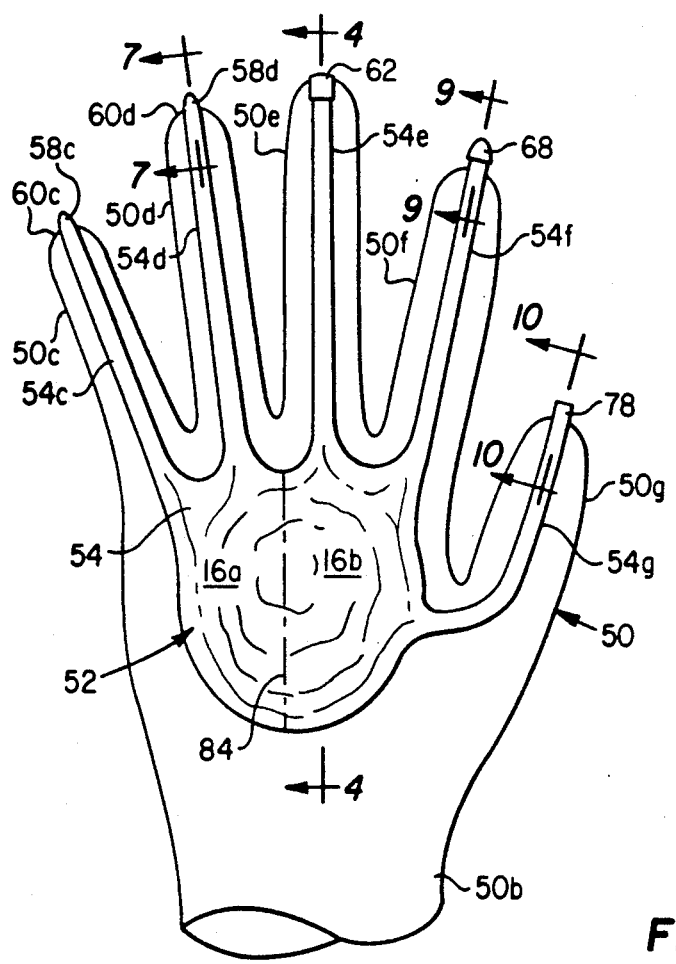
FIG. 2 is a plan view of the palm side of a righthand glove dispenser according to this invention and intended to illustrate that the finger tributaries of a palmar reservoir may terminate in various means for filling the reservoir, means for directing dispensed substance from the glove, or means for both of these purposes.
Figure 8:
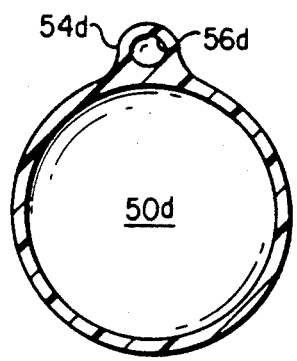
FIG. 8 is an enlarged cross sectional view taken along lines 8—8 of FIG. 7.
Figure 7:
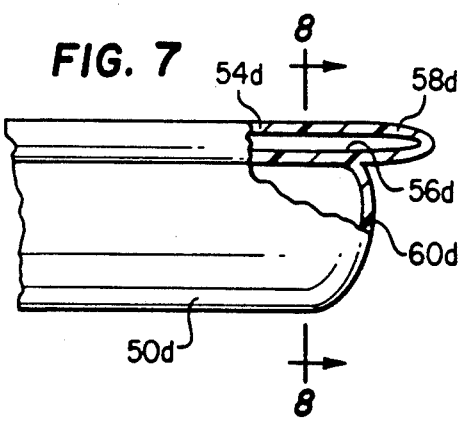
FIG. 7 is an enlarged fragmentary sectional view taken along lines 7—7 of FIG. 2.

Turning now to another embodiment of the dispenser glove which is best illustrated in FIGS. 2 and 4, a righthand glove body 50, similar to the lefthand glove body 20 shown in FIG. 1, displays a reservoir or receptacle 52 overlying the glove palmar area 50a. The glove body 50 also has a wrist embracing portion 50b, finger pockets 50c, 50d, 50e and 50f, a thumb pocket 50g and a back panel 50h. The receptacle 52 is defined by an overlayer or outer face 54 superjacent the glove's palm surface 50a and the inner surfaces of the finger and thumb pockets. The palmar portion 54b of the overlayer 54 is in juxtaposition with the glove palm 50a; and, in this embodiment, the overlayer covers only a central portion of the glove palm area whereby the receptacle 52 is somewhat smaller than that provided in the dispenser glove 20. The overlayer 54 includes elongated finger extensions 54c through 54f and a curved, generally thumb-shaped extension 54g which extend longitudinally along the medial surfaces of the glove finger and thumb pockets 50c through 50g. The finger extensions 54c through 54g are integrally joined, by molding or a similar process, to their associated finger pockets 50c through 50g thereby defining conduits or tributaries leading outwardly from receptacle 52 and traversing the underside of the fingers to, and in some cases beyond, the fingertips of the dispenser glove 50. Finger conduits 56d, 56e, 56f and 56g are identifiable in FIG. 7, FIG. 6, FIG. 9 and FIG. 10, respectively. Each of the conduits provides means to communicate the interior of the receptacle 52 with the distal ends of the finger or thumb extensions for charging or discharging the receptacle as the case may be.

The distal ends of the illustrated conduits 54c through 54g differ in construction and in the manner in which they are employed by the user as material dispensing means. For example, the closed distal ends 58c and 58d of finger extensions 54c and 54d which extend beyond the extreme tip ends 60c and 60d of the finger pockets 50c and 50d may be removed by cutting, puncturing or a similar operation to open these conduits for discharging substance from the receptacle 52.

Figure 6:
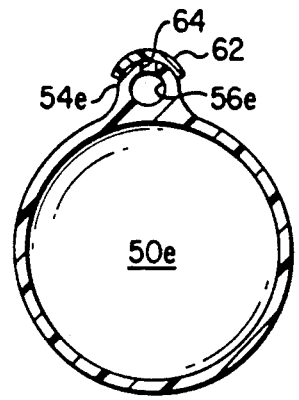
FIG. 6 is an enlarged cross sectional view taken along lines 6—6 of FIG. 4.

FIGS. 4 and 6 best illustrate a tab 62 removably attached to the distal end of the finger extension 54e of the overlayer 54. The tab 62 functions to seal the single discharge aperture 64 opening from finger conduit 56e through the wall of the finger extension 54e. The tab may carry pressure sensitive adhesive for easy detachment and for subsequent resealing of the tab with respect to the extension 54e.

The projecting end of the finger extension 54f comprises a tapered head 66 penetrated by the conduit bore 56f. A flexible closure cap 68 conforming in shape with the head 66 and having a flexible reentrant lip 70 which sealingly embraces the conduit 54f is detachably secured to the head. With the cap 68 removed from the head 66, the conduit bore 56f is open for discharging material from the reservoir 52. A flexible tube 72 having an enlarged receptacle 74 conforming with the closure cap 68 may be pressed into interfitting engagement about the head 66 when the closure cap 68 is removed. With the tube 72 so attached to the head 66, the tube bore 76 provides a highly manipulatable extension of the conduit bore 56f whereby material discharged through the head 66 may be delivered at the remote end of a tube 72 of substantial length.

The thumb conduit bore 56g terminates in a thickened elastic wall 78 comprising the extreme end of the extension 54f. By means of the hollow needle 80 of a typical syringe 82 insertable through the wall 78, dispensable liquids and semisolids may be withdrawn from the receptacle 52 through the conduit 56g or such material may be injected into the receptacle 52 by the same means. The wall 78 is intended to seal itself in a well-known manner after the needle 80 is withdrawn therefrom.

It should be understood that while conduit closures 58c, 58d, 64, 68 and 78 have been depicted and described as illustrative of various types of closure means useful for this purpose, all of the conduits 54c through 54g could be closed by the same type of closure. Alternatively, one or more conduits could be equipped with any of the various closure means described to either discharge or fill or to both discharge and fill the receptacle 52 of the dispenser glove 50.

In FIG. 2, numeral 84 is a phantom line intended to indicate an internal wall or divider that may be provided to partition the receptacle 52 into two isolated compartments wherein different dispensable materials may be stored within the glove 50. Additional dividers, not shown, could be disposed within receptacle 58 if more than two material storage compartments are required in a particular application of the glove 50. It will be understood that the reservoir 22 could be likewise partitioned by an internal wall, not shown.

Turning now to the improved filling means shown in FIGS. 11 through 14, a glove body 90 and an overlayer 94, joined in the same manner as that previously disclosed with respect to glove 20 shown in FIG. 1, define a palmar reservoir 92 and tributary conduits, not shown, extending to the tips of the fingers and thumb pockets 96a and 96b, respectively. The overlayer 94, which is superjacent the palm receptacle 92 and the finger conduits, will be provided with a suitable array of discharge perforations and sealing strips, not shown, as previously disclosed above in connection with glove 20.

While FIG. 11 shows, for the sake of illustration, two distinct means for filling the receptacle 92, it will be understood that one will suffice in actual use. Located in that portion of the overlayer 94 which covers that area of the glove body 90 defining a web 98 between the finger and thumb pockets 96a and 96b is an incision which may be spread apart to form an elongated aperture 100 generally conforming to the curature of the web 98. The extent and shape of the aperture 100 are sufficient to accept any preferred means for directing a flow of dispensable material into the receptacle 92, for example, a funnel or a hose nozzle, not shwon. The closure means for the filling aperture 100 may take the form of a crescent-shaped flap 102 having one edge 104 hinged adjacent to or integrally molded with an edge of the aperture 100. To effect sealing of the filling aperture 100, the closure flap 102, which may be coated with a pressure sensitive adhesive, is drawn completely over the aperture 100 and around the web 98 and thereafter pressed into place as shown in FIG. 12. An extending tab 106 on the flap 102 is not coated with adhesive to facilitate manual grasping and drawing of the flap and to provide a handy means for peeling the flap from the web to reopen the aperture for refilling the reservoir from time to time as needed.

Another filling means for the receptacle 92 which is depicted in FIGS. 11, 13 and 14 includes a integral tubular extension of the overlayer 94 which defines a filling stem 108 having an internal passage 109 which communicates with the receptacle 92 and has a distal end 110 projecting toward the wrist opening of the glove 90. A pressure operated non-return fluid valve 112 of any well-known type is seated in the filling stem 108; and, the distal end 110 of the stem may be conveniently closed by a snap-in type of cap or plug 114 in order to protect the valve 112 from dirt or other contamination. In order that liquid, semisolid and fluid entrained particulate materials may be injected under pressure into receptacle 92 by means of the filling stem 108, it will, in some cases be necessary to vent displaced air from the receptacle to atmosphere to prevent unwanted buildup of back pressure within the receptacle as it is being filled. Such venting could be accomplished by a suitable venting oriface incorporated in the valve 112; or, one or more of the discharge perforations, not shown, through the overlayer 94 could be temporarily uncovered for this purpose.

The glove dispenser 20 depicted in FIG. 1 has no specific means for filling the receptacle 22 and the finger conduits 26c through 26g; however, it will be appreciated that glove 20 may be equipped with either the filling aperture 100 or the filling tube 108 for this purpose. Moreover, a single perforation 30d at the end of the conduit 26d could be utilized for filling purposes in the same manner as the aperture 64 is usable to fill the receptacle 52.

It is contemplated that the glove dispensers shown in FIGS. 1, 2 and 11 may be made by any of several conventional molding and extrusion processes suitable for fabricating thin-walled gloves of the types utilized by homemakers for hand protection, by industrial and laboratory personnel to handle toxic wet and dry material, and by medical personnel to assure sterile handling conditions. It is believed that all of the structural features of the hereindisclosed glove dispensers can be provided in a one-piece glove unit provided that the various overlayers 24, 54 and 94 can be integrally formed superjacent their respective glove bodies. If not, the various overlayers may be separately fabricated for subsequent attachment to an associated glove body by means of a suitable thermal or chemical bonding process.

The number of known materials usable for thin-walled glove fabrication is nearly limitless. Suitable materials may be selected to meet various requirements of a given glove such as strength, elasticity, durability, puncture resistance, permeability, self supportability, chemical resistance, heat resistance, biodegradability, moldability, extrudability, fingertip sensitivity, cost and so forth. A very short list of usable natural and synthetic materials would include natural latex, nitrile compounds, polyurethane coated nylon fabric, synthetic elastomers, polyvinyl chloride (PVC), treated cellulose, and reinforced paper.

From the foregoing detailed description of the hand-worn dispensers shown in FIGS. 1 and 2, respectively, it will be appreciated that each glove includes an overlayer 24 or 54 attached to its underlying glove 20 or 50 to create a material receptacle 22 or 52 and tributary conduits extending from the receptacle along the full length of the glove finers and thumb. Besides this common structural feature, the embodiments charge openings from the receptacle until the glove dispenser user selectively removes some or all of the closures. These common attributes, namely, tributary conduits and selectively removable closures for discharge openings, enable both embodiments of the invention to provide the essential characteristics recited hereinabove, namely, a high degree of user control over both the rate of material discharge and the pattern and directionality of material flow from a glove dispenser.

OPERATION OF THE DISCLOSED EMBODIMENTS

The embodiments of the invention depicted in FIGS. 1 and 2 may be furnished to users with either prefilled or empty substance receptacles. If a prefilled glove or pair of gloves contains sufficient dispensable material to complete an intended operation, no provision need be made for refilling the glove and once emptied it could be discarded. A disposable protective glove of the character shown in FIG. 1 would be well suited for occasional use by gardeners and pet owners for dispensing insecticides, such as flea powder and garden dust, by rubbing or patting the palm of the glove against the plant or the animal to be treated to induce material flow from the palmar receptacle 20 and further conduits 26c through 26g. It will be understood that the user may adjust the flow rate and flow pattern of insecticide material from the glove by peeling away only selected ones or all of the various strips which originally securely seal all of the performations opening from the receptacle and finger conduits. Moreover, by removing only certain seal strips at one time and others later, the pattern and rate of material discharge may be advantageously modified as the operation procedes. For example, in applying insecticide to small animals it would be advantageous to keep all seal strips in place except those covering the fingertip area of the glove so that the user might compress the receptacle and finger conduits to eject powder in small quantities and in a highly controlled manner about the animal's face and into its ears. A higher discharge rate could be easily provided merely by peeling off the remaining seal strips covering the thumb and finger conduits. Powder dispensed at such higher rate could be easily and efficiently applied to the animal's legs and tail by grasping the same and traversing the glove therealong. Finally, to treat the back and sides of the animal, all of the seal strips covering the palmar receptacle 22 could be removed to maximize the rate of powder flow and to enlarge the area of the flow pattern from the glove. At the end of the treating operation, it is contemplated that the prefilled glove would be disposed of in any safe manner; therefore, such disposable gloves could be fabricated of reinforced or treated paper or other inexpensive material suitable for single usage.

If, on the other hand, a hand-worn dispenser is intended for commercial use on a frequent basis, it could be made of a tough, wear-resistant material that would permit repeated glove reuse by veterinarians, stockmen, animal groomers and the like. Such a reusable glove should have suitable receptacle and conduit recharging means incorporated directly in the glove structure. Either the aperture 100 and coacting closure flap 102 or the filling stem 108 could be used to introduce powdered substance into the interior receptacle of glove 20 and such substance would flow easily from the receptacle into the finger conduits due to the substantial cross sectional area of these conduits. The filling aperture 100 could be gravity fed; however, use of the filler stem 108 would require that a resupply of powder be entrained in a low pressure air stream.

The foregoing example teaches that the aggregate material flow from the dispenser can be regulated by removing selected seal strips covering perforations through the glove overlayer 24. This invention also contemplates that these perforations vary in diameter and interspacing in such a way that some portions of the perforation pattern will dispense material at a different rate than others. For example, the index finger conduit perforations could be larger and more closely spaced than the middle fingers conduit perforations, whereby a stroke of the index finger over a surface would deliver more dispensable substance than would a stroke of the middle finger. It will also be apparent that the glove 20 can be made to have all or only a portion of the overlayer perforated by variable size perforations in variable numbers and in variable patterns. As mentioned earlier, the seal strips which provide means for regulating the material flow from the dispenser glove can be of any desired shape, size and number. If only two seal strips covered all of the perforations, a coarse two level flow rate control would be provided. A multiplicity of small seal strips each covering only a few of many perforations would enable a user to closely regulate flow over the available range in small increments. Likewise the shape and location of the flow pattern from the palmar and finger perforations could be carefully controlled.

While the example first given above describes a hand-worn dispenser suitable for applying dry, particulate material, it is well within the capability of the embodiment shown in FIG. 1 to store and dispense semiliquid, viscous substances; provided, that the uncovered perforations through the overlayer 24 are sized to allow the substance to flow therethrough only when the receptacle or the conduits are intentionally pressed or squeezed by the user. Lubricating grease, thick paint, spreadable adhesive, medicinal ointment, gelatinous skin lotion and hair shampoo are but a few of the many semiliquid materials which could be commercially packaged inside a glove which conveniently stores the product and also provides a hand-worn dispenser having simple and easy-to-use means for regulating the material's rate of flow and its pattern and direction of flow as it exits the glove.

While the previously discussed embodiment of the invention shown in FIG. 1 is well-adapted for storing and dispensing particulate and semiliquid material, the embodiment illustrated in FIGS. 2, 4 and 6 through 9 is specially adapted for dispensing material in liquid and semiliquid states. It will be noted that the glove 50 has a smaller receptacle 52 located in the cup of the hand and that the tributaries of the receptacle have a rather small bore, seen at 56d and 56f, which connects the receptacle directly to the tip area of the fingers and thumb. There are no perforations opening at any point through the overlayer 54 except the dispensing-filling aperture 64 at the extreme end of finger extension 54e. Instead, one or more of the distal or finger tip ends of the conduits are provided with means for discharging material from the glove 50. It is contemplated that, instead of rubbing or patting the glove upon a surface to effect material discharge, the user will slightly bend or double his hand to apply a squeezing force to the receptacle whereby material will be urged under pressure from the receptacle through the conduits and then ejected from the open distal ends of one or more conduits.

In FIG. 2, for purposes of illustration only, various means for closing or terminating the ends of the conduits have been shown on the fingertips of a single glove 50. The application and advantages of those various conduit terminations will be discussed in detail hereinafter.

The receptacle 52 of glove 50 may be filled with liquid or semiliquid substances by means of a filler stem attached to the receptacle 52 in a similar manner that stem 108 is attached to the receptacle 94 of glove 90. Air displaced from receptacle 52 upon its being filled could be conveniently directed through a vent like aperture 64 at the distal end of one of the finger conduits. After filling is completed, the vent 64 would be closed by an appropriate selfadhering seal like tab 62. Alternately, liquid could be injected into a distal end of one of the conduits by any one of means shown in FIG. 2. Thus a suitable injection nozzle, not shown, could be pressed into the aperture 64 in conduit 54e; the tube 72 when attached to the head 66 could be used to convey substances from a source, not shown, to the conduit bore 56f; and, substance could be injected through a hollow tube 80 penetrating the elastic wall 78 closing the distal end of conduit bore 56g. It will be appreciated that a selected one of the just described receptacle filling means could be located at the distal end of any selected conduit rather than in the specific location shown in FIG. 2. It will also be apparent that the receptacle 52 could be entirely filled by injecting liquid directly through the receptacle wall 54b by means of a hypodermic needle or the like; provided, the material from which the overlayer 54 is made is self sealing after being punctured.

Should all of the fingers of a glove 50 be equipped with conduit closures like 58c and 58d in FIG. 2, the rate of fluid discharge and the array or pattern of fluid distribution outside the glove will be determined by how many and which of the closures are cut off or punctured. This kind of conduit closure is best suited to applications where all of the liquid contained in the glove will be dispensed during a single usage; and, the glove will be disposed of rather than refilled. Applying shampoo to the hair of humans or animals followed by washing the same with the glove-protected hand or hands could comprise such an application. Another exemplary application comprises dispensing medicated substance from the fingertips of a glove in a non-contacting, shower-like manner and at a user controlled rate upon a portion of a human body traumatized by burning, scraping or the like. Such a glove dispenser should be initially sterilized and packaged in a sterile condition for subsequent use in a routine medical procedure or in an emergency setting. The glove may be prefilled with a desired medication and used as a storage container; or, in case the medication does not store well, the glove could include one of the filling means depicted in FIGS. 9, 10 and 13 whereby the receptacle is filled just before the medication is dispensed from the glove.

The conduit closure tabs 62 could be employed to better advantage in place of the just-described cutoff type conduit terminations 58c and 58d if it is desired to store an unused portion of the initial supply of substance in the receptacle to accommodate subsequent usages of the glove. Thus a tab 62 could be partially peeled away to expose the discharge aperture 64 while fluid is being dispensed from the glove; and, each tab could be repositioned over its associated aperture when a dispensing episode is terminated. Repeated opening and reclosing of one or more discharge apertures at the glove fingertips would be the expected mode where the glove is used to store and periodically dispense such frequently used substances as furniture and automobile polish, liquid dishwashing detergent, suntan and sunscreen lotions, insect repellant, semiliquid solder flux and a myriad of other domestically and industrially used liquid and semiliquid substances.

Figure 9:
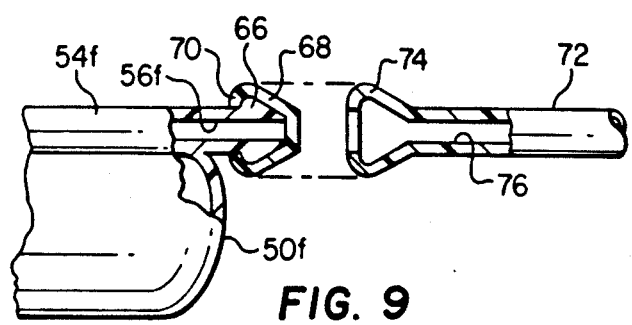
FIG. 9 is an enlarged fragmentary sectional view taken along lines 9—9 of FIG. 2 depicting a partially sectioned fragment of a feed/discharge tube connectable to a terminal fitting of a finger tributary.

The auxillary filling-dispensing attachment shown in FIG. 9 is intended for highly specialized uses of a hand-worn dispenser. As noted above, the closure cap 68 may be removed to open the conduit bore 56f for either dispensing substance from the glove receptacle 52 or for filling the receptacle as needed. The attachable tube 72 permits the user to direct dispensed substance to locations remote from the glove fingertip such as hard-to-reach lubricating points and fittings inside a machine. The tube also permits quick and efficient filling of the glove at a location remote from that where a substance is stored in order to maintain the substance sterile or under pressure or at a given temperature until just before the glove is filled for dispensing the substance.

Since only one conduit temination of the type shown in FIG. 9 is likely to be used with a given glove, the user will be able to develope a rather high discharge pressure through the single conduit bore 56f by exerting maximum compressive force on the palmar receptacle 52. Such high discharge pressure will propel the dispensed substance, especially thin liquids, from the distal end of the glove finger with considerable force and directionality. This directional liquid jetting action achievable simply by the user's pointing the glove finger and bending his hand could be employed to great advantage in such widely diverse applications as irrigating burned tissue and other open wounds with an antiseptic liquid solution to squirting various cleaning solutions against mirrors, windows, tile shower enclosures and the like.

Another special adaptation of this invention is achieved by the internal partition 84 shown in FIG. 2 which divides the receptacle 52 into plural compartments 16a and 16b for the purpose of storing substances in each compartment. Any of the hereinbefore described terminations at the distal ends of the receptacle tributary conduits may be utilized for filling the plural compartments and dispensing substances therefrom. The same substance could be stored in each of the compartments 16a and 16b to provide discrete measured quantities or doses to be dispensed or administered at intervals. Various formulations such as two-part adhesives and certain hair dyes require that mixing of their ingredients be delayed until the formulation is put to use. Such ingredients could be stored in an unmixed condition in a partitioned glove and dispensed in the order desired for mixing just prior to use. It will also be appreciated that the ingredients of such formulations could be stored separately in the unpartitioned receptacles of a pair of dispenser gloves and that mixing of ingedients could take place within one of the receptacles following injection of an ingredient from one glove to the other by a suitable interaction of filling and dispensing means described above.

The foregoing description of the embodiments of the invention shown in the drawings is illustrative and explanatory only; and, various changes in the size, shape and materials, as well as in specific details of the illustrated construction, may be made without departing from the scope of the invention. Therefore, I do not intend to be limited to the details shown and described herein, but intend to cover all changes and modifications which are encompassed by the scope and spirit of the appended claims.

What I claim as my invention is:

1. A fingered glove defining a pocket for receiving a wearer's hand; a palmate overlayer joined about its entire marginal edge to the exterior plamar side of said glove to define therebetween a sealed material receptacle generally overlying the glove palm and further defining plural imperforate material discharge conduit means in communication with said receptacle; each of said conduits means extending longitudinally along the palmer side of a different glove finger and having a sealed distal end projecting beyond the distal end of the glove finger it extends along; and, the distal ends of said conduit means being selectively severable to vary the material discharge rates and patterns through the distal ends of said conduit means.

* * * * *

UNITED STATES PATENT AND TRADEMARK OFFICE
CERTIFICATE OF CORRECTION

PATENT NO. :   5,169,251

DATED      :   December 8, 1992

INVENTOR(S) :  Sharron L. Davis

It is certified that error appears in the above-identified patent and that said Letters Patent is hereby corrected as shown below:

Column 8, line 54, after "embodiments" insert-- 20 and 50 are each provided with closures for all plural dis- --.

Signed and Sealed this

Twenty-sixth Day of October, 1993

Attest:

BRUCE LEHMAN

Attesting Officer        Commissioner of Patents and Trademarks